(12) United States Patent
Zhao et al.

(10) Patent No.: US 8,933,031 B2
(45) Date of Patent: Jan. 13, 2015

(54) POLYPEPTIDE INHIBITING ANGIOGENESIS AND APPLICATION THEREOF

(75) Inventors: Hui Zhao, Shanghai (CN); Xun Xu, Shanghai (CN)

(73) Assignee: Shanghai First People's Hospital, Shanghai (CN)

( * ) Notice: Subject to any disclaimer, the term of this patent is extended or adjusted under 35 U.S.C. 154(b) by 363 days.

(21) Appl. No.: 12/866,166

(22) PCT Filed: Feb. 4, 2008

(86) PCT No.: PCT/CN2008/070285
§ 371 (c)(1),
(2), (4) Date: Oct. 26, 2010

(87) PCT Pub. No.: WO2009/100617
PCT Pub. Date: Aug. 20, 2009

(65) Prior Publication Data
US 2011/0034387 A1    Feb. 10, 2011

(51) Int. Cl.
*A61K 38/00*    (2006.01)
*C07K 14/78*    (2006.01)
*C07K 14/775*   (2006.01)

(52) U.S. Cl.
CPC .............. *C07K 14/775* (2013.01); *A61K 38/00* (2013.01)
USPC ....... 514/13.3; 514/21.7; 514/18.7; 514/19.3; 514/20.8

(58) Field of Classification Search
None
See application file for complete search history.

(56) References Cited

U.S. PATENT DOCUMENTS

| | | | | |
|---|---|---|---|---|
| 5,801,146 A | * | 9/1998 | Davidson | 514/13.3 |
| 6,576,609 B1 | | 6/2003 | Soff et al. | |
| 6,743,428 B1 | * | 6/2004 | Chang et al. | 424/185.1 |
| 2006/0246084 A1 | * | 11/2006 | Brubaker et al. | 424/184.1 |

FOREIGN PATENT DOCUMENTS

| | | |
|---|---|---|
| CN | 1223690 | 7/1999 |
| WO | 97/41824 | 11/1997 |

OTHER PUBLICATIONS

Vihinen-Ranta et al. (Eur J Biochem 1997).*
Peter Carmeliet, Nature Medicine vol. 9, Jun. 2003, pp. 653-660.*
Rheumatoid Arthritis (RA), Merck, Accessed Feb. 14, 2014.*
IBD Merck, Apr. 2013 by Walfish.*
Infertility Feb. 2013 Merck by Rebar.*
Brain tumor, Jun. 2013 Merck by Patchell.*
International Search Report of PCT/CN2008/070285, dated Nov. 6, 2008.
Kim et al., "Human apolipoprotein(a) kringle V inhibits angiogenesis in vitro and in vivo by interfering with the activation of focal adhesion kinases," Biochemical and Biophysical Research Communications, vol. 313, 2004, pp. 534-540.
Zhao et al., "A synthetic peptide selected by bioinformatics inhibits mouse corneal neovascularization," Chin J Ophthalmol, vol. 43, No. 2, 2007, pp. 151-157, and English language abstract thereof.

* cited by examiner

*Primary Examiner* — James H Alstrum Acevedo
*Assistant Examiner* — Li Lee
(74) *Attorney, Agent, or Firm* — Hamre, Schumann, Mueller & Larson P.C.

(57) ABSTRACT

Provided is a low molecular polypeptide that can inhibit angiogenesis consisting of amino acid sequence YRGKKA, which is same to one portion sequence in apolipoprotein (a) Kringle V. Also provided are pharmaceutical composition and the uses for preventing or treating diseases relating to angiogenesis.

7 Claims, 2 Drawing Sheets

POLYPEPTIDE INHIBITING ANGIOGENESIS AND APPLICATION THEREOF

TECHNICAL FIELD

The present invention relates to bio-pharmaceutical field. In particular, the present invention relates to novel polypeptides for preventing and treating angiogenesis, which are small molecules and called as "AU6". The present invention further relates to a method for preparing the polypeptides, use of said polypeptides, and a pharmaceutical composition comprising the polypeptide.

TECHNICAL BACKGROUND

Angiogenesis is a course of the growth of a new blood vessel in the existing vascular system. It is a necessary physiological change in embryonic development, wound healing, tissue regeneration and tissue repair. However, it is also a pathological basis for many systemic and topical diseases. Said systemic diseases include neovascular eye diseases, tumor angiogenesis, rheumatic arthritis, psoriasis, etc.

Angiogenesis involves a complicated course with multiple steps, including proliferation, migration and invasion of vascular endothelial cell and formation of lumen, etc. Angiogenesis is strictly controlled by the balance between proangiogenic factors and anti-angiogenic factors. Breaking said balance may initiate a cellular signal of angiogenesis, leading to pathological neovascular generation. Vascular endothelial growth factor (VEGF) is a central induction mediator of this complicated angiogenesis cascade, which specifically acts on the vascular endothelial cell.

Human VEGF gene consists of 8 exons and 7 introns, with a length of about 14 kb. The VEGF family contains at least 4 members due to different splicing modes of RNA, which are $VEGF_{121}$, $VEGF_{165}$, $VEGF_{189}$, and $VEGF_{206}$. The $VEGF_{165}$ is the primary isomer.

The neovascular eye diseases are a type of diseases causing blindness with high incidence which have wide destructiveness and may involve the whole eyeball, including age-related macular degeneration, diabetic retinopathy, corneal infection, and neovascular glaucoma. Lesions secondary to ocular neovascularization, such as bleeding, exudation and fibrosis, also seriously affect the vision quality and the quality of life of the patient. However, methods for treating these kinds of diseases currently are limited, the effects are not so fine, and the safety needs to be further confirmed.

When developing effective inhibitors of neovascularization, the specificity of the ocular drugs should be sufficiently considered.

Firstly, there are many anatomical and functional barriers in eyes. Systemic administration usually cannot produce topically sufficient drug concentration in ocular tissue due to the blood-aqueous humor barrier and blood-retina barrier. In topical administration, such as injection in vitreous cavity, the macromolecule larger than 76.5 kDa theoretically is difficult to penetrate the retina to act on the retinal and choroidal neovascularization.

Secondly, the solubility of the drugs in the hydrophilic tears, aqueous humor, and vitreous humor is positively correlated to their effects.

Thirdly, for the above major reasons, the bioavailability of ocular drugs is very low. To improve it, the concentration of drugs administered may be increased. However, compounds for treating neoplastic neovascularization exhibit obvious toxicity, so that high dose cannot be used in either systemic or topical administration.

Fourthly, currently a series of relatively safe endogenous inhibitors of neovascularization, such as angiostatin consisting of plasminogen Kringle domains 1-4, have been demonstrated to obviously inhibit growth of vessel blood-dependent tumor. However, due to their relative large molecular weight and complicated spatial conformation, these inhibitors have disadvantages, such as complicated recombinant expression and purification processes in preparation, residual endotoxin and so on.

Therefore, there is an urgent need in developing inhibitors of neovascularization, which are small molecules, safe and effective, and compatible with eyeball tissues.

SUMMARY OF INVENTION

The purpose of the present invention is to provide a small molecular polypeptide, AU6 polypeptide, and fragments, analogs, and derivatives thereof, which are compatible with eyeball tissue, effective and safe, and could inhibit angiogenesis.

The other purpose of the present invention is to provide a method for preparing said polypeptide and use of said polypeptide.

In the first aspect, the present invention provides a polypeptide represented by the following formula I, or a pharmaceutically acceptable salt thereof, wherein, Xaa0 is not present, or a peptide segment consisting of 1-3 amino acids;

Xaa1 is selected from the group consisting of Tyr or Phe;

Xaa2 is selected from the group consisting of Arg or Lys;

Xaa3 is selected from the group consisting of Gly or Ala;

Xaa4 is selected from the group consisting of Lys or Arg;

Xaa5 is selected from the group consisting of Lys or Arg;

Xaa6 is selected from the group consisting of Ala, Val, Leu or Ile;

Xaa7 is not present, or a peptide segment consisting of 1-3 amino acids;

and said polypeptide exhibits an activity of inhibiting angiogenesis.

In another preferred embodiment, Xaa0 and Xaa7 are not present.

In another preferred embodiment, Xaa2 is Arg, Xaa4 is Lys, and Xaa5 is Lys.

In another preferred embodiment, said polypeptide is selected from the group consisting of:

(a) a polypeptide having the amino acid sequence represented by YRGKKA(SEQ ID NO:1);

(b) a polypeptide which is derived from the polypeptide of (a) by substitution, deletion, or addition of one to two amino acids in the amino acid sequence of SEQ ID NO: 1 and which has the activity of inhibiting angiogenesis.

The present invention further provides a dimer form and a polymer form of compound of formula I, which exhibit the activity of inhibiting angiogenesis.

In the second aspect, the present invention provides an isolated nucleic acid molecule encoding the above-mentioned polypeptide of the present invention.

In the third aspect, the present invention provides a pharmaceutical composition comprising:

(a) the above-mentioned polypeptide or a pharmaceutically acceptable salt thereof of the present invention; and (b) a pharmaceutically acceptable carrier or excipient.

In another preferred embodiment, the dosage form of the composition is eyedrop, injection solution (such as injection solution for using around or inside the eye), and ophthalmic gel or eye ointment.

In another preferred embodiment, the composition is in a slow release dosage form.

In the fourth aspect, the present invention provides a use of said polypeptide or a pharmaceutically acceptable salt thereof for preparing a medicament for inhibiting angiogenesis, or preventing or treating diseases associated with angiogenesis.

In another preferred embodiment, the disease associated with angiogenesis is selected from the group consisting of neovascular eye diseases, tumor, ischemic heart disease, non-inflammatory myocardiopathy, coronary sclerosis, arteriosclerosis obliterans, artery embolism, artery thrombus, Berger's disease, chronic inflammation, inflammatory intestinal diseases, ulcer, rheumatic arthritis, scleroderma, psoriasis, infertility and sarcoma-like diseases.

In another preferred embodiment, the neovascular eye diseases include diseases involved in choroid, retina, cornea or iris, including age-related macular degeneration, proliferative diabetic retinopathy, retinal vessel-blocked diseases, retinopathy of prematurity, corneal infection, and neovascular glaucoma.

In the fifth aspect, the present invention provides a method for inhibiting angiogenesis in mammal, comprising the step of administering a subject in need thereof with the polypeptide or a pharmaceutically acceptable salt thereof of the present invention.

In another preferred embodiment, the subject is a human.

In another preferred embodiment, the angiogenesis is associated with neovascular eye diseases.

DESCRIPTION OF DRAWINGS

The following descriptions of drawings are to illustrate the specific embodiments of the present invention. They should not be construed as limiting the scope of the present invention, which should be defined by the claims.

MODES FOR CARRYING OUT THE PRESENT INVENTION

After extensive and thorough study, the inventor firstly prepares small molecular polypeptides which exhibit a function of inhibiting angiogenesis and have a molecular weight of less than 1 kD (for example, just about 720 D). In particular, by utilizing the method of bioinformatics, the inventor selected several candidate sequences based on the homology analysis and analysis on the biological properties. After synthesizing these sequences via solid phase synthesis, these sequences were screened in the vascular model of chick embryo chorioallantoic membrane, the corneal angiogenesis model of VEGF-induced mice, and the retinal angiogenesis model of hypoxia-induced mouse. Thus, a class of novel, small molecular polypeptides exhibiting the function of preventing and treating angiogenesis were obtained, which were called as AU6.

The small peptides AU6 of the present invention have a small molecular weight. They can penetrate through various ocular tissue barriers. They have good water solubility, so that they can maintain a relatively high concentration in neutral tears, aqueous humor and vitreous humor. They are highly safe with a minor toxicity to the biological tissue. The bioavailability in eye topical administration is very high, thus the dose can be reduced, and hence the systemic toxicity can also be reduced. Based on the above work, the inventor finishes this invention.

Active Polypeptides

In the present invention, the terms "the polypeptide(s) of the present invention", "AU6 polypeptide(s)", "AU6 small peptide(s)", "short peptide(s) AU6" and "peptide(s) AU6" can be used interchangeably. All of them refer to the protein or polypeptide having peptide AU6 amino acid sequence (SEQ ID NO: 1) exhibiting an activity of inhibiting angiogenesis. In addition, said terms comprise the variants of SEQ ID NO: 1 sequence which exhibit the function of inhibiting angiogenesis. These variations include, but are not limited to, deletions, insertions and/or substitutions of 1-5 amino acids (typically 1-4, preferably 1-3, more preferably 1-2, most preferably 1), and addition of one or more amino acids (typically less than 5, preferably less than 3, more preferably less than 2) at C-terminus and/or N-terminus. For example, the protein's functions are usually unchanged when an amino residue is substituted by a similar or analogous one. Further, the addition of one or several amino acids at C-terminus and/or N-terminus generally will not change the structure and function of protein. The terms also include the monomer and polymer of the polypeptide of the present invention.

The present invention further includes the active fragments, derivatives and analogs of AU6 polypeptide. As used herein, the terms "fragments", "derivatives" and "analogs" refer to the polypeptides basically maintaining the function or activity of inhibiting angiogenesis. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of AU6 polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6H is. According to the subject application, these fragments, derivatives and analogs are within the scope commonly known by the skilled person.

A class of preferred active derivatives is the polypeptides formed by replacing at most 5, preferably at most 3, more preferably at most 2, most preferably 1 amino acid of the amino acid sequence represented by formula I with the amino acid having similar or analogous property. These conservative variant polypeptides are preferably formed by carrying out the amino acid replacement according to Table I. A class of preferred polypeptide derivatives is showed in SEQ ID NO: 3.

TABLE I

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of AU6 polypeptide. These analogues can differ from naturally occurring AU6 polypeptide by amino acid sequence differences or by modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acetylation, or carboxylation. Also included is modification of glycosylation, e.g., the polypeptides made by subjecting to the glycosylation modification during its synthesis and processing or in the further processing steps. These modifications can be accompanied by exposing the polypeptide to enzymes which affect glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention could be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals, such as sodium, potassium, calcium or magnesium, and esters, carbamate or other conventional "prodrug" forms.

Encoding Sequences

The present invention further relates to a polynucleotide encoding AU6 polypeptide. A preferred encoding sequence is TACCGGGGCAAGAAGGCA (SEQ ID NO: 2).

The polynucleotide of the present invention can be in a form of DNA or RNA. DNA can be the coding strand or the non-coding strand. The coding sequence encoding the mature polypeptide can be identical to the coding sequence indicated in SEQ ID NO: 2, or can be a degenerate variant thereof. As used herein, "degenerate variant" refers to a nucleic acid sequence which encodes the protein having the amino acid sequence of SEQ ID NO:1, but has a nucleic acid sequence different from the corresponding coding sequence in SEQ ID NO: 2.

The whole length of AU6 nucleotide sequence or fragment thereof of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by the vector or the coding sequence of the AU6 polypeptide of the present invention.

In another aspect, the present invention further comprises a polyclonal antibody or monoclonal antibody, especially the monoclonal antibody, having specificity to the polypeptide encoded by AU6 DNA or fragment thereof.

Preparation Method

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes under room temperature to remove the Fmoc protective groups. Then the sequence is extended from the C-terminus to the N-terminus according to the predetermined amino acid sequence. After synthesis, trifluoroacetic acid containing 4% p-methylphenol is used to cleave the preinsulin-related peptide from the resin and the protective groups are removed. The resin can be filtered, and the crude peptide can be obtained via precipitation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine(DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular screen Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the polypeptide AU6 of the present invention is prepared by solid phase method according to its sequence, purified by high performance liquid chromatography, thereby obtaining freeze-dried powder of target peptide with high purity. The powder is stored at −20° C.

Another method is to produce the polypeptide of the present invention by a recombinant technique. With the conventional recombinant DNA technique, the polynucleotide of the present invention can be used to express or produce recombinant AU6 polypeptides. Generally, the method comprises the following steps:

(1) Transforming or transfecting a suitable host cell with a polynucleotide or variant thereof encoding the AU6 polypeptide of the present invention or a recombinant expression vector containing said polynucleotide;

(2) Culturing the host cell in a suitable culture medium;

(3) Isolating and purifying protein from the culture medium or cell.

The recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

It is also contemplated to link multiple polypeptides of the present invention in series due to their short length. After recombinant expression, the expression product is obtained in a form of polymer. Then the polymer is enzymatically cleaved to form the desired small peptides.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof, and (b) a pharmaceutically acceptable carrier or excipient. The amount of the polypeptide of the present invention generally is 10 μg to 100 mg per dose, preferably 100-1000 μg per dose.

For the purpose of the invention, the effective dose is to administer an individual about 0.01 mg to 50 mg of the polypeptide of the present invention per kg body weight, preferably 0.05 mg to 10 mg of the polypeptide of the present invention per kg body weight. Further, the polypeptide of the present invention can be used alone, or in combination with the other therapeutic agents (for example, formulating into the same pharmaceutical composition).

The pharmaceutical composition can further comprise a pharmaceutically acceptable carrier. The term "pharmaceutically acceptable carrier" refers to the carrier for using in administering the therapeutic agents. The term refers to such medical carriers that they themselves do not induce antibody deleterious to the subject having been administered the composition, and they do not have excessive toxicity after administration. These carriers are well known by the skilled person in the art. And detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise solution, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulating the composition of the present invention, it can be administered via conventional routes, including but are not limited to, administering on ocular surface, around the eye, intra-ocular, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include eyedrop, injection, ophthalmic gel, and eye ointment.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulating can be carried out in a conventional manner according to the dosage form.

For example, formulation of eyedrop can be done as follows: dissolving short peptide AU6 or a pharmaceutically acceptable salt thereof and the basic substances in sterile water (surfactant is dissolved in said water), adjusting osmotic pressure and alkalinity acidity to the physiological level, optionally adding suitable medical additives, such as preservatives, stabilizing agents, buffering agents, isotonicities, anti-oxidants and tackifiers, and then allowing them completely dissolved.

The pharmaceutical composition of the present invention can further be administered in a form of slow release agent. For example, the short peptide AU6 or salt thereof can be incorporated into the pill or microcapsule with the slow release polymer as the carrier, and then the pill or microcapsule is implanted into the tissue to be treated by operation. Furthermore, the short peptide AU6 or salt thereof can be used by insertion of intra-ocular lens coated with said drugs beforehand. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples of the slow release polymer include the biodegradable polymers, such as polymer of lactic acid, and lactic acid-glycolic acid copolymer.

When the pharmaceutical composition of the present invention is used in the actual treatment, the dose of the short peptide AU6 or a pharmaceutically acceptable salt thereof, as an active ingredient, can be suitably determined according to the body weight, age, sex, symptom of each patient. For example, when topically dropping in the eye, the concentration of the active ingredient generally is 0.1-10 wt %, preferably 1-5 wt %, for 2-6 times per day and 1-5 drops each time.

Industrial Applicability

The pharmaceutical composition containing the peptide of the present invention or a pharmaceutically acceptable salt thereof as an active ingredient exhibits significant inhibition activity on angiogenesis. As verified by in vivo animal tests, the polypeptide of the present invention not only can inhibit angiogenesis in chick embryo chorioallantoic membrane, but also can inhibit corneal angiogenesis in the VEGF-induced mice and the retinal angiogenesis in the hypoxia-induced mice.

The main advantages of the present invention include:

(a) The polypeptide of the present invention has small molecular weight, so it can penetrate ocular tissue barrier;

(b) The polypeptide of the present invention has good water solubility, so it can maintain relatively high concentration in neutral tears, aqueous humor and vitreous humor;

(c) The polypeptide of the present invention has high safety with less toxicity to the tissue of the organism;

(d) The polypeptide of the present invention can be synthesized via solid phase synthesis with high purity, high yield and low cost.

Therefore, the polypeptide of the present invention can be developed into a medicine for treating neovascular eye diseases and related diseases associated with angiogenesis, such as tumor angiogenesis, etc.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Synthesis of Polypeptide

The AU6 polypeptide represented by SEQ ID NO: 1 was synthesized by the commercially available SYMPHONY polypeptide synthesizer, comprising the following steps:

1. Formulating, according to calculation of software, the desired protective amino acid solutions, condensation agents, cleaving agents, and adding sufficient amounts of DMF, DCM into the corresponding bottles of the instrument;

2. Adding 100 μmol FMOC-Ala-Wang-Resin into a reactor;

3. Placing a 15 mg centrifuge tube on the conduit for collecting the cleaving solution;

4. Editing the program, generally the swelling time for the resin was 30 minutes, the time for de-protection was 5 minutes, 15 minutes for two times, the condensation time was 30 minutes, and the cleavage procedure lasted 2 hours;

5. Operating the synthesizer and performing the synthesis according to the program;

6. Precipitating the cleaving solution with ether, centrifuging, blow drying, and purifying by HPLC.

120 mg polypeptide AU6 was obtained, which was a white powder (with good water solubility) with purity of >95%. The polypeptide was sealed and stored at −20° C. ready for use.

EXAMPLE 2

Effect of AU6 on Angiogenesis in Chick Embryo Chorioallantoic Membrane

1. Material and Method 1.1 Material: Whatman filter paper was purchased from SIGMA Corporation, USA.

1.2 Preparation of Model and Intervention Test: The chick fertile eggs of 1-2 days old were randomly grouped into 3 groups, which were respectively a control group, a 10 μg AU6 intervention group, and a 50 μg AU6 intervention group, with 9-15 eggs for each group. The surface of the fertile eggs was cleansing with tap water, and then the eggs were soaked in 0.2% benzalkonium bromide (bromo-geramine) solution for 5-10 minutes. The eggs were placed with the blunt end upward, and hatched in an incubator under 37° C. and 60-70% humidity. The eggs were overturned for at least two times per day, and were hatched for 5 days with 24 hours as one day. Under sterile condition, a small hole of about 1-2cm$^2$ was created at the blunt end (air chamber end) with a nipper. The eggshell membrane and air chamber were successively revealed and the chorioallantoic membrane with blood vessel was exposed. Whatman filter papers with a diameter of 5mm were used as a sample carrier, each of which adsorbed 5 μl of PBS solution containing 0 μg, 10 μg or 50 μg of AU6. After air drying, the papers were placed into the center of the chorioallantoic membrane. The little window was sealed with plastic adhesive tape. And the eggs were hatched under the same conditions as described above for 2 days.

1.3 Counting the Number of Micrangiums in the Chorioallantoic Membrane: the adhesive tape was removed, and the micrangiums newly generated on the chorioallantoic membrane were observed. The number of micrangiums (with diameter no greater than 10 μm) within 5 mm around the filter paper for each group was counted under stereomicroscope.

1.4 Statistical Analysis: The experimental data were represented as x̄±s. The numbers of micrangiums in the chick embryo chorioallantoic membrane for each group were compared by one-way ANOVA. P<0.05 indicates statistical significance.

2. Results

Figure 1:
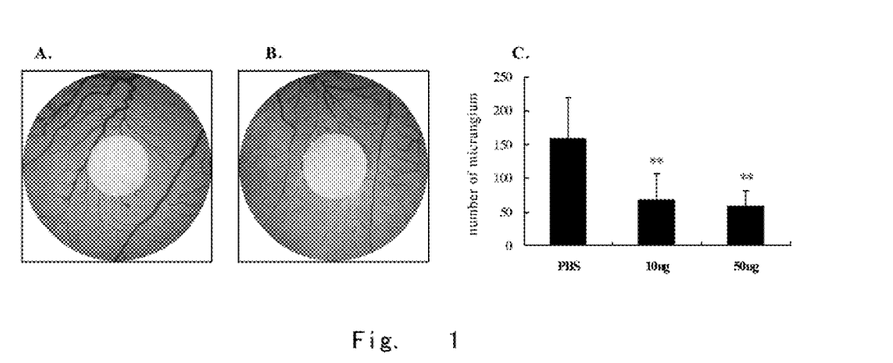
FIG. 1 indicates the effect of AU6 polypeptide on angiogenesis in chick embryo chorioallantoic membrane. Panel A indicates the angiogenesis in the chorioallantoic membrane in the PBS group. Panel B indicates the angiogenesis in the chorioallantoic membrane in the 50 μg AU6 intervention group. Panel C indicates the number of micrangium in each group of chick embryo chorioallantoic membrane, wherein n=9-15, **p<0.01 as compared with the PBS group.

Within 5 mm around the filter paper on the chick embryo chorioallantoic membrane of the fertile eggs, the blood vessel of the fertilized chick embryo chorioallantoic membrane in the PBS control group has a lot of micrangiums branched from the larger blood vessel progressively, while the numbers of micrangiums in the AU6-treated groups were significantly less than the normal group. The toxicity of AU6 to the chick embryo was not observed (FIGS. 1A, 1B and 1C).

EXAMPLE 3

Effect of AU6 on Angiogenesis in the Cornea of Mouse Induced by VEGF

1. Materials and Methods 1.2 Experimental Animal and Material: Healthy, male C57B1/6 mice of 5-6 weeks old weighing about 20 g were purchased from Laboratory Animal Center of Chinese Academy of Sciences. Sucrose octasulfate-aluminum complex was purchased from Sigma-Aldrich, USA. PolyHEMA (poly (2-hydroxyethylmethacylate)) was purchased from Aldrich, USA. And human recombinant VEGF$_{165}$ was purchased from SIGMA, USA.

1.2 Preparation of Model and Intervention Test: 12% Poly-HEMA in an ethanol solution was mixed with an equal volume of normal saline solution containing sucrose octasulfate-aluminum complex powder, thus forming blank slow-release particles with a volume of 0.35 mm*0.35 mm*0.20 mm. 160 ng of VEGF and different amounts (0 µg, 1.0 µg, 2.0 µg) of the small peptides were added into said particles. The resultant products were stored at −20° C., ready for use. The above operations were done under a sterile condition. Thirty C57B1/6 mice (30 eyes) were randomly grouped into a control group (VEGF group), VEGF+1.0 µg AU6 group, and VEGF+2.0 µg AU6 group, with 10 eyes for each group. Under a sterile condition, 23G syringe needle was used to perform blunt separation between the layers of the corneal stroma in the experimental eyes, so as to form a pouch of 0.5 mm*0.5 mm. The particles containing 160 ng VEGF and different amounts of small peptides were implanted into the pouches in the ocular cornea in the mice of each group, and were made to have a distance of 0.6-0.8 mm from limbus. After operation, 0.5% aureomycin oculentum was applied to the eyes to prevent infection and reduce irritation. Photos were obtained 7 days after operation to observe the growth of newly generated blood vessel in the cornea, and a histopathological examination was performed concurrently.

1.3 Quantitative Measurement of Corneal Neovascularization: the length of the new blood vessels grown from limbus was measured 7 days after operation. The area of the new blood vessel was calculated based on the longest blood vessel which had less continuous bending and which grew toward the slow release particles. Formula is as follows: Area (mm$^2$) =0.5*π*VL (mm)*CN*0.4 (mm), wherein VL is the length of the longest new blood vessel grown from limbus to the cornea (maximal vessel length), and CN represents the clock hours of corneal neovascularization (the cornea is dividing into clock hours).

1.4 Qualitative Observation of Corneal Neovascularization: Each group of animals was sacrificed by excessive anaesthesia 7 days after operation. The eyeballs were obtained under a sterile condition, and fixed in 10% neutral formaldehyde, and then subjected to histopathological examination. The samples were embedded within paraffin and cut into 3 µm sections, HE stained, and observed under light microscope.

1.5 Statistical Analysis: The experimental data were represented as x̄±s. The length of the longest new blood vessel in cornea, clock hours and area for each group were compared by one-way ANOVA. P<0.05 indicates statistical significance.

Figure 2:
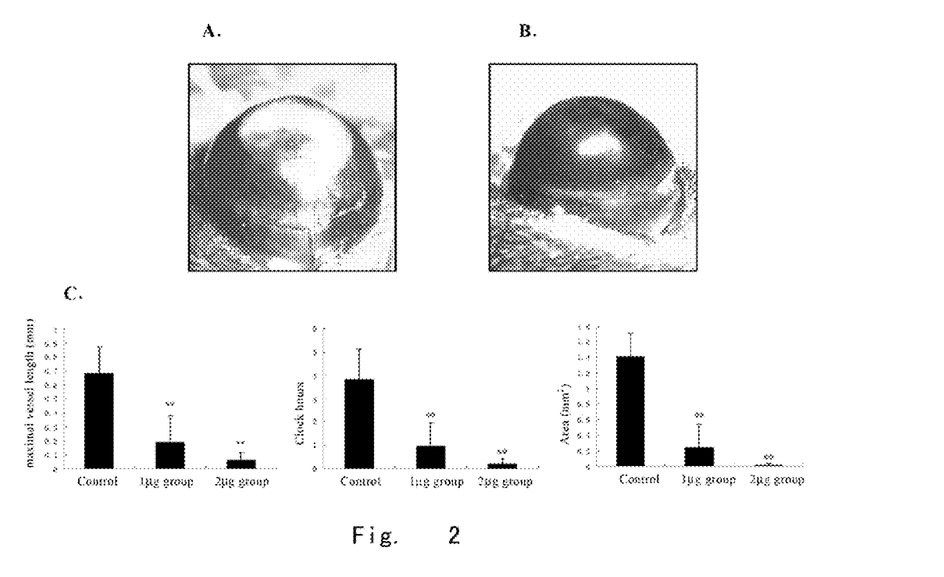
FIG. 2 shows the effect of the AU6 polypeptide on angiogenesis in the mouse cornea induced by VEGF. Panel A indicates the result of angiogenesis in the cornea induced by VEGF. Panel B indicates the result of angiogenesis in the cornea after treating with 2.0 μg AU6. Panel C shows the length of the longest newly generated blood vessel in the cornea, the clock hours of corneal neovascularization, and area in each group, wherein n=10, **p<0.01 as compared with the control group.

2. Results 2.1 Quantitative Measurement of Corneal Neovascularization: The corneal neovascularization in the C57B1/6 mice implanted with particles in the layers of corneal stroma was observed and it was found that there were new blood vessels grown from limbus 3 days after operation and reached peak 7 days after operation. Seven days after operation, there were significant decrease in the longest blood vessel length of the new blood vessel, the clock hours of corneal neovascularization and the area of blood vessel in the AU6 intervention groups as compared with the control group (FIGS. 2A, 2B and 2C).

2.2 Histopathological Examination on the Corneal Tissue: Seven days after operation, in the control group, the corneal tissue had oedema, the epithelial layer and the endodermis maintained intact, the arrangement of the stroma layer was loose, and there were many blood capillary lumens, as observed by HE stained sections. In the AU6 intervention group, there were no obvious oedema in the corneal tissue, the epithelial layer and the endodermis maintained intact, the arrangement of the stroma layer was relatively regular, and very few blood capillary lumens were observed. The toxicity of AU6 to each layer of corneal tissues was not observed.

EXAMPLE 4

Effect of AU6 the Retinal Neovascularization Induced by Anoxia

1. Materials and Methods 1.1 Materials and Main Devices: Healthy, neonatal C57B1/6 mice, 7 days age, weighing about 4 g were purchased from Laboratory Animal Center of Chinese Academy of Sciences. The sex of the mice was not limited. FITC-dextran (molecular weight about 2*10$^6$) was purchased from SIGMA, USA.

1.2 Preparation of Model and Intervention Test: Neonatal mice of 10 nests were randomly grouped into 5 groups, which respectively were oxygen group, oxygen plus PBS group, oxygen plus 5 µg AU6 group, oxygen plus 10 µg AU6 group, and control group, with 10-11 mice for each group. Seven days after birth, except the control group, all of the other groups of mice were placed in an airproof drying cabinet together with their mother mice of the same nest. Wet pure oxygen was introduced into the drying cabinet, and the oxygen concentration in volume was maintained as 75%±5%. The oxygen concentration was measured every 3-6 hours by using oxygen meter. The control group was incubated normally in air. Twelve days after birth, 0.5 µl PBS solution containing respectively 0, 5 µg, and 10 µg AU6 were injected into the vitreous chambers of the mice in the oxygen plus PBS group and in the oxygen plus AU6 group (5 µg, and 10 µg).

1.3 FITC-dextran Retinal Angiography and Flat-mounts: Seventeen days after birth, 50 mg/ml FITC-dextran solution were perfused into the left ventricle of mice in each group. Then the eyeballs immediately were obtained, fixed in paraformaldehyde solution for 5-24 hours at 4° C. And then the retinas were isolated and flat-mounted. The morphological change of the retinal blood vessel was observed under fluorescence microscope.

1.4 Quantitative Measurement of Retinal Neovascularization: The animals in each group were sacrificed by excessive anaesthesia 17 days after birth. The eyeballs were obtained, and fixed in 10% neutral formaldehyde, and then subjected to histopathological examination. The samples were embedded within paraffin and cut into 6 µm continuous sections. The direction of slicing was the sagittal direction, i.e., the direction went through the cornea and was parallel to the optic nerve. The sections were subjected to HE stain. Five sections were randomly selected for each eye except the sections containing a broken optic nerve. The numbers of the nucleus of the vascular endothelial cells which broke through the retinal inner limiting membrane were counted under light microscope.

1.5 Statistical Analysis: The experimental data were represented as x̄±s. Non-paired t test was used to compare the oxygen group and control group. The numbers of the nucleus which broke through the retinal inner limiting membrane in the AU6-treated group and the oxygen group were compared by one-way ANOVA. P<0.05 indicates statistical significance.

Figure 3:
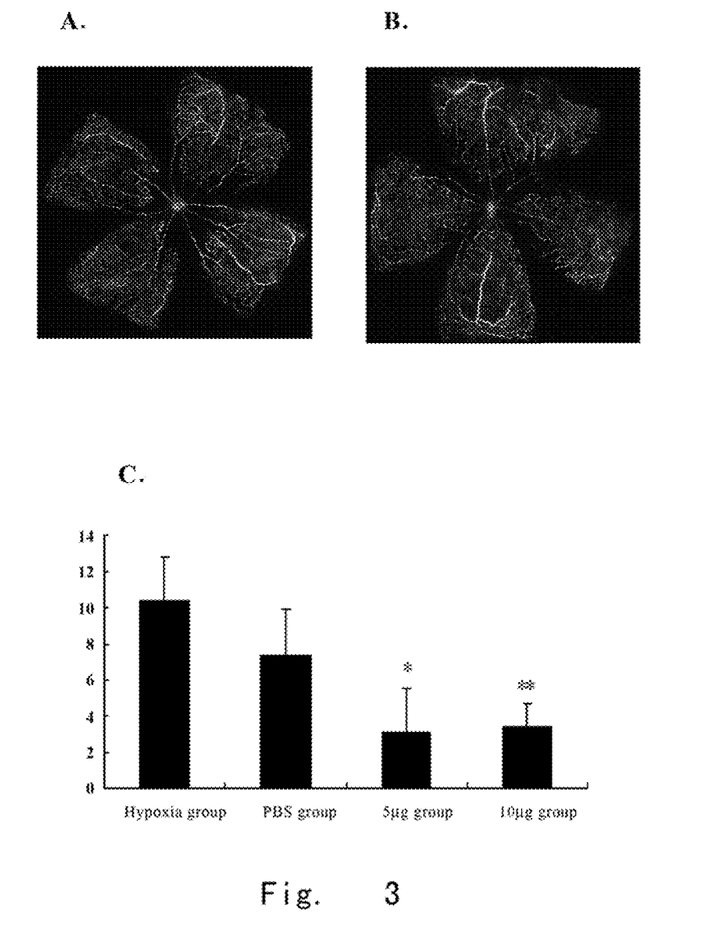
FIG. 3 shows the effect of the AU6 polypeptide on angiogenesis in the retina of the anoxic mouse. Panel A shows the flat-mounts of retinal angiography in the oxygen group. Panel B shows the flat-mounts of retinal angiography in the 10 μg AU6-treated group. Panel C shows the numbers of the nucleus of the vascular endothelial cells in each group which break through the retinal inner limiting membrane, wherein n is 10, *p<0.05, **p<0.01, as compared with the oxygen group.

2. Results 2.1 FITC-dextran retinal angiography and flat-mounts: No non-perfusion area and neovascular cluster were observed in the mice in the normal control group. The retinal flat mounts of the model-treated group showed a wide range of non-perfusion area and many neovascular clusters. The flat amounts of the AU6-treated group showed that the non-perfusion area was narrowed, and the neovascular clusters were reduced (FIGS. 3A and 3B).

2.2 Quantitative Measurement of Retinal Neovascularization: Only a few nucleus of vascular endothelial cells which broke through the inner limiting membrane were observed in the retinal sections of mice in the normal control group. The retinal sections of the model-treated group showed that the number of nucleus of vascular endothelial cells which broke through the inner limiting membrane were obviously greater than those of the normal group. The retinal sections of the AU6-treated group showed that the nucleus of vascular endothelial cells which broke through the inner limiting membrane were obviously less than those of the model-treated group. AU6 toxicity to each layer of retinal tissues was not observed (FIG. 3C).

EXAMPLE 6

Preparation of Eyedrop

The following components were mixed via the conventional techniques to obtain an 1% eyedrop, the formulation of which was as follows:

| | |
|---|---|
| AU6 peptide | 10 mg |
| Hydroxylpropyl methylcelloluse | 0.03 g |
| Sterile water | q.s. to 10 ml |

The osmotic pressure was adjusted to 300 Osm, and the pH was adjusted to 6.8-7.1.

Three volunteers used the eyedrop for one week, two times per day, and 2 drops/eye for each time. The results showed that the eyedrop could inhibit ocular angiogenesis.

Discussion

The AU6 polypeptide of the present invention exhibited significant activity of inhibiting angiogenesis, which was demonstrated by the following: AU6 could inhibit angiogenesis in chick embryo chorioallantoic membrane, AU6 could inhibit corneal angiogenesis in VEGF-induced mice, and AU6 could inhibit retinal angiogenesis in hypoxia-induced mice.

With respect to the sequence, the amino acid sequence of AU6 represented by SEQ ID NO: 1 was identical to the fragment containing 6 amino acid residues in apo(a) KV.

Kringle domain is a conservative structure consisting of about 80 amino acids, which comprises 3 pairs of disulfide bonds, and forms a double ring configuration. It is an independent folded unit exerting the biological functions. The Kringle domain is present in various proteins which have different functions, such as growth factors, proteases and coagulation factors. The Kringle domain plays an important role in the specific interaction between proteins and in their regulation. Studies showed that many Kringle domains, such as angiostatin, plasminogen kringle 5, could block angiogenesis.

In the proteins containing Kringle domain, apolipoprotein (a) (apo(a)) is a glycoprotein with a molecular weight in the range from 400 kDa to 800 kDa, which links to apoB-100 via disulfide bond to form lipoprotein(a). Studies showed that apo(a)-transgenic mouse had regressive LL/2 tumor in vivo due to reduced microvessel density, which demonstrated that apo(a) could inhibit angiogenesis in vivo. The apo(a) is highly homologous to plasminogen. It comprises several Kringle areas (Kringle IV, KIV) which are randomly repeated and similar to plasminogen Kringle 4 (K4). These areas are named successively as KIV-1 to KIV-10, followed by one Kringle V (KV) domain which is homologous to plasminogen K5, and a protease-like area.

The AU6 polypeptide of the present invention is identical to a fragment containing 6 amino acids in apo(a) KV, indicating the importance of said short peptide sequence in inhibiting angiogenesis. This also indicates that genes of apo(a) and plasminogen may be derived from the same precursor, wherein the conservative sequence exhibiting potential biological activity plays a key role in maintaining the protein function.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

What we claimed are:

1. A polypeptide represented by the following formula I, or a pharmaceutically acceptable salt thereof,

[Xaa0]-[Xaa1]-[Xaa2]-[Xaa3]-[Xaa4]-[Xaa5]-[Xaa6]-[Xaa7]   (I)

wherein,
Xaa0 is not present, or a peptide segment consisting of 1 amino acid;
Xaa1 is selected from the group consisting of Tyr or Phe;
Xaa2 is Arg;
Xaa3 is selected from the group consisting of Gly or Ala;
Xaa4 is Lys;
Xaa5 is Lys;
Xaa6 is selected from the group consisting of Ala, Val, Leu or Ile;
Xaa7 is not present, or a peptide segment consisting of 1 amino acid;
said polypeptide exhibits an activity of inhibiting angiogenesis,
with the proviso that YRGKKA (SEQ ID No:1) is excluded.

2. A pharmaceutical composition comprising:
(a) the polypeptide of claim 1 or a pharmaceutically acceptable salt thereof; and
(b) a pharmaceutically acceptable carrier or excipient.

3. The pharmaceutical composition of claim 2, wherein an amount of the polypeptide is 10 μg to 100 mg per dose.

4. The pharmaceutical composition of claim 2, wherein a dosage form of the composition is an eyedrop, an injection solution, an ophthalmic gel or an eye ointment.

5. A method of preparing a medicament, comprising: adding the polypeptide of claim 1 or a pharmaceutically acceptable salt thereof and a pharmaceutically acceptable carrier or excipient to a mixture, wherein the polypeptide of claim 1 or a pharmaceutically acceptable salt thereof is added in an amount effective for inhibiting angionenesis or treating a disease associated with angionenesis in a subject in need thereof.

6. The use of claim 5, wherein the disease associated with angiogenesis is selected from the group consisting of neovascular eye diseases, tumors, ischemic heart disease, non-inflammatory myocardiopathy, coronary sclerosis, arteriosclerosis obliterans, artery embolism, artery thrombus, Berger's disease, chronic inflammation, inflammatory intestinal diseases, ulcer, rheumatic arthritis, scleroderma, and psoriasis.

7. A method for inhibiting angiogenesis in a mammal, comprising the step of administering a subject in need thereof with the polypeptide of claim 1 or a pharmaceutically acceptable salt thereof.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: Peptide AU6 for inhibiting angiogenesis

<400> SEQUENCE: 1

Tyr Arg Gly Lys Lys Ala
1               5

<210> SEQ ID NO 2
<211> LENGTH: 18
<212> TYPE: DNA
<213> ORGANISM: Artificial Sequence
<220> FEATURE:
```

```
<221> NAME/KEY: misc_feature
<223> OTHER INFORMATION: Coding sequence of AU6 polypeptide

<400> SEQUENCE: 2
taccggggca agaaggca                                                 18

<210> SEQ ID NO 3
<211> LENGTH: 6
<212> TYPE: PRT
<213> ORGANISM: Artificial Sequence
<220> FEATURE:
<221> NAME/KEY: misc_feature
<223> OTHER INFORMATION: Derivative polypeptide of AU6
<220> FEATURE:
<221> NAME/KEY: misc_feature
<222> LOCATION: (1)..(1)
<223> OTHER INFORMATION: Xaa=Y, or F
<220> FEATURE:
<221> NAME/KEY: misc_feature
<222> LOCATION: (2)..(2)
<223> OTHER INFORMATION: Xaa=R, or K
<220> FEATURE:
<221> NAME/KEY: misc_feature
<222> LOCATION: (3)..(3)
<223> OTHER INFORMATION: Xaa=G, or A
<220> FEATURE:
<221> NAME/KEY: misc_feature
<222> LOCATION: (4)..(4)
<223> OTHER INFORMATION: Xaa=K, or R
<220> FEATURE:
<221> NAME/KEY: misc_feature
<222> LOCATION: (5)..(5)
<223> OTHER INFORMATION: Xaa=K, or R
<220> FEATURE:
<221> NAME/KEY: misc_feature
<222> LOCATION: (6)..(6)
<223> OTHER INFORMATION: Xaa=A,V,L, or I

<400> SEQUENCE: 3

Xaa Xaa Xaa Xaa Xaa Xaa
1               5
```